United States Patent [19]

Roman

[11] 4,122,606
[45] Oct. 31, 1978

[54] METHOD AND APPARATUS FOR MOUNTING DENTAL DIE MODELS IN DENTAL STONE

[76] Inventor: Richard C. Roman, 230 Westmoreland Dr., Vernon Hills, Ill. 60060

[21] Appl. No.: 708,641

[22] Filed: Jul. 26, 1976

[51] Int. Cl.² ............................................. A61C 13/00
[52] U.S. Cl. ......................................................... 32/11
[58] Field of Search ...................... 32/11, 2, 40 R, 71; 249/54; 425/171; 164/376

[56] References Cited

U.S. PATENT DOCUMENTS

| | | | |
|---|---|---|---|
| 2,337,036 | 12/1943 | Erdle | 249/54 |
| 3,436,827 | 4/1969 | Dew | 32/11 |
| 3,470,614 | 10/1969 | Kelly | 32/11 |
| 3,581,398 | 6/1971 | Thomas | 32/11 |
| 3,932,939 | 1/1976 | Weissman | 32/11 |
| 3,952,415 | 4/1976 | Samuel | 32/11 |

OTHER PUBLICATIONS

"Locate Dowel Pins Accurately", by Dowoloczstor, J. Aderer Inc., 21-24, 44th Ave, Long Island City, N.Y. 11101.

*Primary Examiner*—Robert Peshock
*Attorney, Agent, or Firm*—Garrettson Ellis

[57] ABSTRACT

Dental die models may be mounted in dental stone by filling a flexible tray having sides with uncured, fluid dental stone, and inserting the outer ends of dowel pins of the die models into the stone, while it still is in fluid condition. If more than one die model is inserted into the stone in the tray, the stone may be divided by inserting stiff divider partitions before curing. After curing, the stone is removed by flexing the tray, after which the stone may be broken along the divider partitions into separate pieces, and ground to a shape to fit in an articulator, or the like. Colored indicating members may be used to indicate the location of the outer ends of the dowel pins for grinding. Permanently emplaced portions of the die model may carry dowel pins having heads on their outer ends.

15 Claims, 5 Drawing Figures

METHOD AND APPARATUS FOR MOUNTING DENTAL DIE MODELS IN DENTAL STONE

BACKGROUND OF THE INVENTION

In dentistry, die models of teeth and jaw portions are often used for making complex prosthodontic appliances, such as bridgework, crowns, and the like. This is accomplished by making an impression mold out of a quick-setting impression material around the actual teeth of the patient, thus duplicating the patient's anatomical structure. Thereafter, models of the teeth and jaw portions are reproduced from the impression, which is then utilized in the building of the dental prosthesis.

In a typical procedure, after preparation of the model, several dowel pins, typically made of brass, are inserted into the base of the model to permit the cutting of various portions of the model into sections, at least one dowel pin fitting into each section.

To facilitate the cutting of the model into sections, prior to cutting, in conventional practice, the model is placed onto a mass of partially cured dental stone which has been formed into a lump on a flat surface, and is of about the consistency of dough. The dowel pins are forced into the dental stone, and the bottom surface of the model rests on the upper surface of the dental stone. Thereafter, the dental stone is allowed to harden, after which it is ground into an appropriate configuration for being received by an articulator, usually roughly approximately the shape of the die model, for duplication of jaw action as the dental prosthetis is built on the model.

After hardening of the stone, the model can be cut into various separate sections as desired. The model is generally treated with a separating medium (releasing agent) to prevent adhesion to the dental stone. Accordingly, the individual separated portions of the model, each carrying one or more dowel pins, can be selectively removed from the mass of stone and the rest of the model, for work. Thereafter, it may be replaced, being positioned and retained by the one or more dowel pins attached to it by reinsertion of the dowel pins into their holes in the dental stone, to precisely reposition the separate model portion with respect to the rest of the model.

The above conventional prior art technique of preparing dental models for work is tedious and time consuming, requiring considerate skill in the proper preparation of a hand-shaped mass of dental stone for receiving the model.

Also, in this technique, one must be very careful to avoid creating bubbles in the uncured dental stone adjacent to the dowel pins, or under the model, which, of course, would reduce the firm mounting of the model in the stone.

Furthermore, the working time of the dental stone, being partially cured to the consistency of dough when it is generally worked and shaped, may be undesirably short under certain circumstances. This may result in the need to reprepare the dental stone, and repeat the operation.

Furthermore, problems exist, in that it is often desirable to permanently retain some portions of the model in the stone, when there is no need to remove it, to avoid the possibility that those portions of the model may accidentally fall out or get lost. On the other hand, other portions of the model should be removable, as described above.

Another problem that arises in the grinding of the dental stone to fit articulator: if one accidentally grinds the end of a dowel pin, which is typically made of brass or other soft alloy, the end of the dowel pin may be flared outwardly by the force of the grinding. Thus it becomes impossible to remove from the stone the particular section of the model to which that dowel pin is attached without laborous further grinding and cutting away (or rebending) of the accidentally flared end of the dowel pin.

DESCRIPTION OF THE INVENTION

In accordance with this invention, the above problems are solved by the utilization of the novel method and apparatus of this invention. By this invention, the operation of mounting a dental model into stone is significantly facilitated and placed on a more reliable, accurate, footing, where the possibilities of error are reduced. Also, the operation is placed on a more routine and semi-automatic basis, so that it can be performed by less highly skilled personnel than the prior art techniques.

In accordance with this invention, dental die models are mounted on dental stone by the method which comprises the following steps:

A flexible tray having sides is filled, typically to the brim, with uncured, fluid dental stone, to provide a mass of dental stone of a predetermined depth which is generally equal to or slightly greater than the length of the dowel pins protruding out of the bottom face of the dental model.

Dental models, carrying dowel pins, which have generally been treated with a separating solution (release agent), are placed into contact with the surface of the dental stone, inserting the dowel pins projecting from the die models into the still-fluid stone.

The dental stone is thereafter allowed to harden, after which the flexible tray is flexed to remove the dental stone from it for grinding of the dental stone to fit an articulator, or other use.

A major advantage of the invention of this application is that the walls of the flexible tray provide side support to the dental stone. Accordingly, the dowel pins and die models may be placed in the dental stone while the stone is still in a fluid condition: i.e. not self-supporting in the manner of a dough-like consistency, being retained by the walls of the flexible tray.

Because of this, the dental stone has a greatly reduced voscosity while being worked, when compared with the prior technique of using dough-like, self-supporting dental stone on a flat surface. Thus, it becomes much easier to remove bubbles from adjacent the dowel pins and underneath the model which, if present, can spoil the work.

The dowel pins can serve as a vertical support, if desired, for the dental model, the dowel pins resting against the bottom of the tray. The height of the walls of the tray may be proportioned to match the length that the dowel pins protrude from the underside of the dental mode, typically from one-half to one inch, including the colored indicating and spacing members which may be carried by the pins as described below.

It is possible, for purposes of increased efficiency, to mount several die models at once in the same tray of dental stone in accordance with this invention. The die models may be spaced from each other in the tray. Stiff divider partitions, made of plastic or other material which is not adherent to the dental stone, may be inserted as partitions into the tray between the various models. Accordingly, after the dental stone has hardened, the tray may be flexed to remove the dental stone from it, and the dental stone may be broken along the divider partitions into separate pieces, separating the die models from each other.

As another aspect and advantage of this invention, outer ends of the dowel pins may be covered with a colored indicating and spacing member. This may be done by dipping the ends of the dowel pins into a solution of colored vinyl plastisol resin, dissolved in a volatile solvent; or a small closed-end tube of plastic may be slipped over the dowel pins; so that the outer end of the dowel pin is covered with a plastic indicator member, which preferably has a thickness of at least 2 or 3 mm. Accordingly, upon the grinding of the dental stone into a desired shape to be received by an articulator, or any other desired shape, the appearance of the colored indicating member indicates the proximity of the dowel pins without accidentally damaging the pins. Accordingly, the user is warned, and can terminate grinding before damaging the dowel pins. Also, the colored member provides a little extra grinding space to adjust the plane of occlusion of the model without damaging the dowel pins.

Also, if desired, dowel pins carried by portions of the die model which are not intended to be removable from the stone for work may carry enlarged retention heads on their outer ends, which may resemble a nail head or the like. This causes the portions of the die model which are held by these particular dowel pins to be permanently retained in the dental stone.

In the drawings, FIG. 1 is a perspective view of a typical dental die model for mounting on dental stone, showing its dowel pins, some of which carry at their ends the colored indicating member of this invention, and others of which carry enlarged heads.

Figure 1:
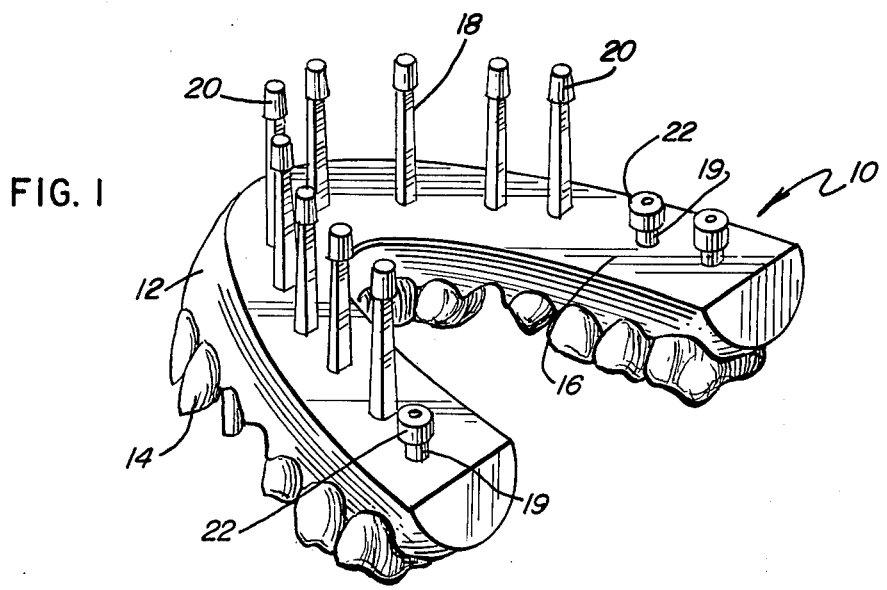

Referring to FIG. 1, a die model 10 is shown, anatomically duplicating a portion of the upper jaw 12 and the teeth 14 carried thereby. The rear surface 16 of the die model may have been flattened by grinding or the like, and holes have been drilled into the rear surface of the die model to receive a plurality of dowel pins 18, 19 which have conventional threaded portions screwed into the die model.

Some of the dowel pins 18 carry colored indicating and spacing members 20, made of a sleeve of transparent, colored plastic or the like, which may be placed over the outer ends of the dowel pins as shown. Other of the dowel pins 19 typically do not carry colored indicating and spacing members, but exhibit flat heads 22 at their ends, to facilitate their permanent retention in the dental stone.

Figure 2:
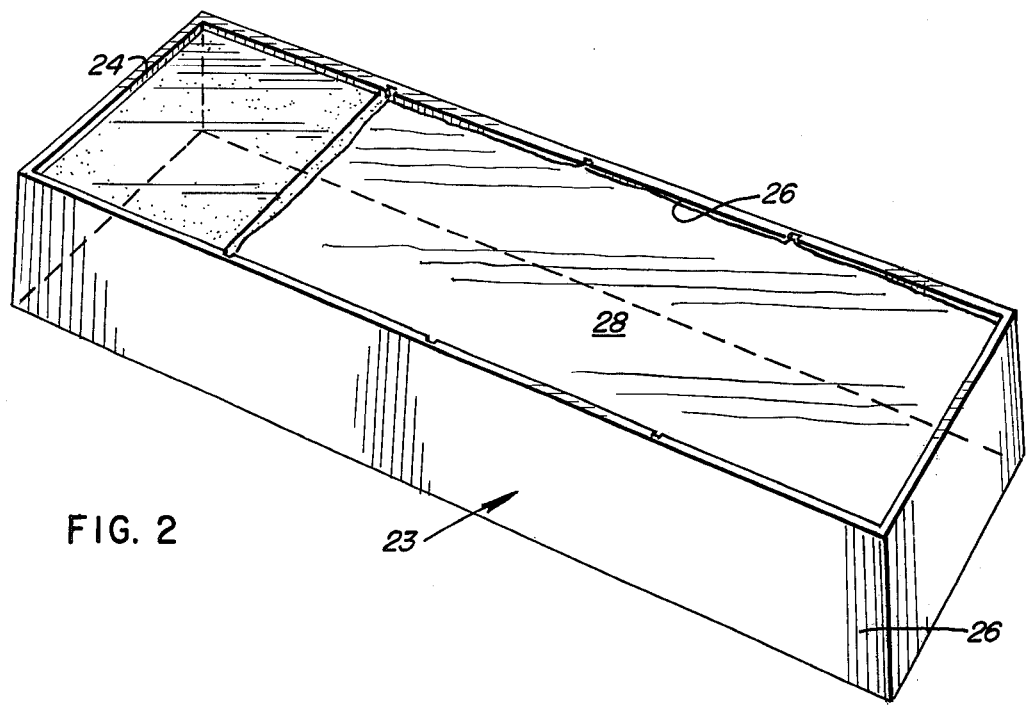
FIG. 2 is a perspective view of the flexible tray of this invention, filled to the brim with dental stone. A portion of the tray is filled with a divider block, to avoid wastage of dental stone.

FIG. 2 shows a flexible tray made of rubber or the like, in accordance with this invention, which may be generally rectangular in its inner shape.

One or more divider blocks 24 may be inserted into the tray to reduce its volume as desired. In the specific embodiment shown, three die models are to be processed in accordance with this invention, while the specific tray 23 has room for the processing of four normally-sized die models. Accordingly, a single divider block 24, occupying one-fourth of the volume of the contents of the tray, may be inserted.

Tray 23 defines walls 26, so that the tray may be filled with uncured, fluid dental stone 28 to a predetermined depth, which is typically the same as the length that dowel pins 18 and the indicating-spacing members 20 protrude outwardly from rear surface 16 of the die model 10. Typically, the length of protrusion of dowel pins 18 and indicating-spacing members 20, is adjusted to be essentially uniform.

Figure 3:
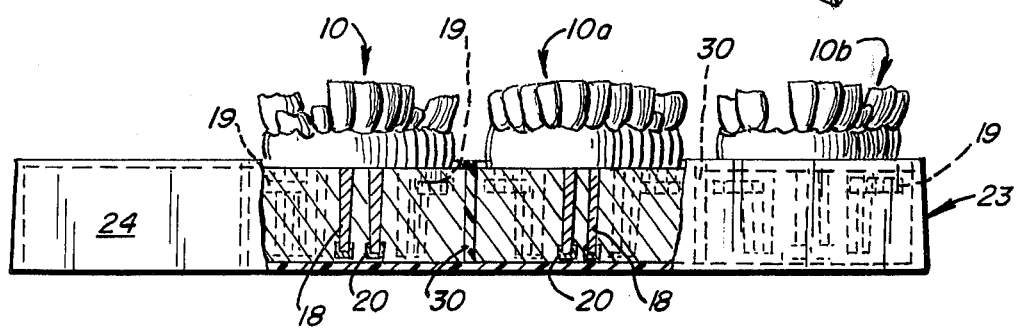
FIG. 3 is an elevational view of FIG. 2, with portions broken away, showing three dental models mounted in the dental stone, and showing rectangular divider members between the models.
Figure 4:
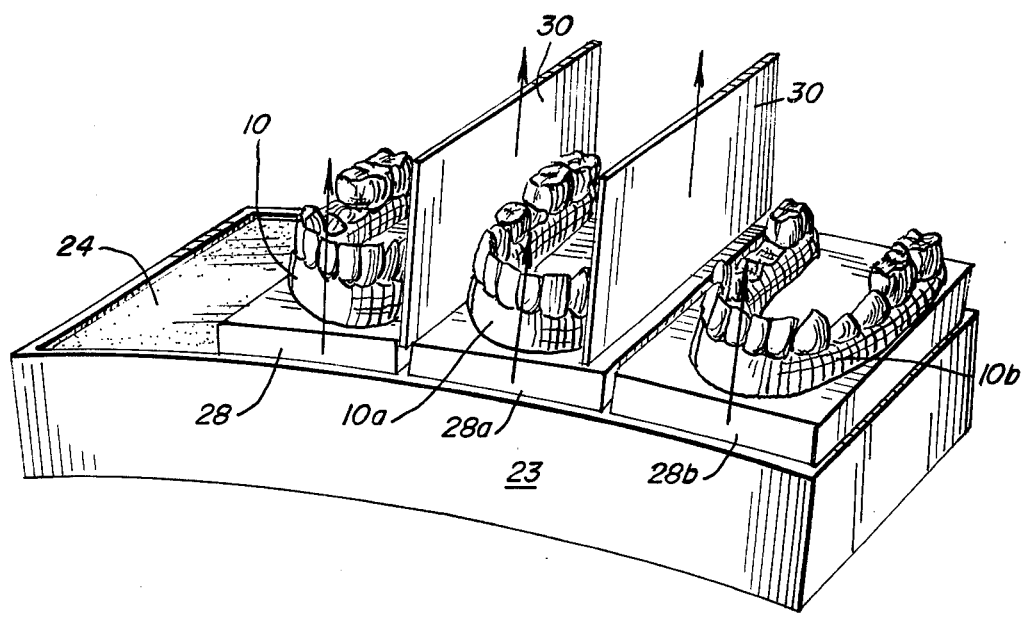
FIG. 4 is a perspective view showing the removal of the cured stone and the models carried thereon from the tray of FIG. 3, the stone being separated into sections along the divider members.

After tray 23 has been filled with dental stone 28, typically to the brim as shown in FIG. 2, and the dental stone is smoothed off with a straight edge, the die model 10, plus other, similar die models, 10a, 10b, may be placed on the tray by pressing of rear surface 16 against the exposed surface of fluid dental stone 28, while inserting dowel pins 18, 19 into the dental stone. This is shown in FIG. 3. Indicating-spacing members 20 are thus positioned at the bottom of the dental stone in tray 23 and dowel pins 18 thus support die model 10 in the liquid dental stone, to prevent its sinking too deeply.

Stiff divider partitions 30 may be placed into the dental stone between models 10, 10a and 10b. These divider partitions are generally thin, rectangular sheets, made of a plastic material which is relatively nonadherent to the dental stone, and proportioned to the shape of a cross section of the inner portion of tray 23.

Thereafter, the structure is allowed to stand until the dental stone has hardened.

Figure 5:
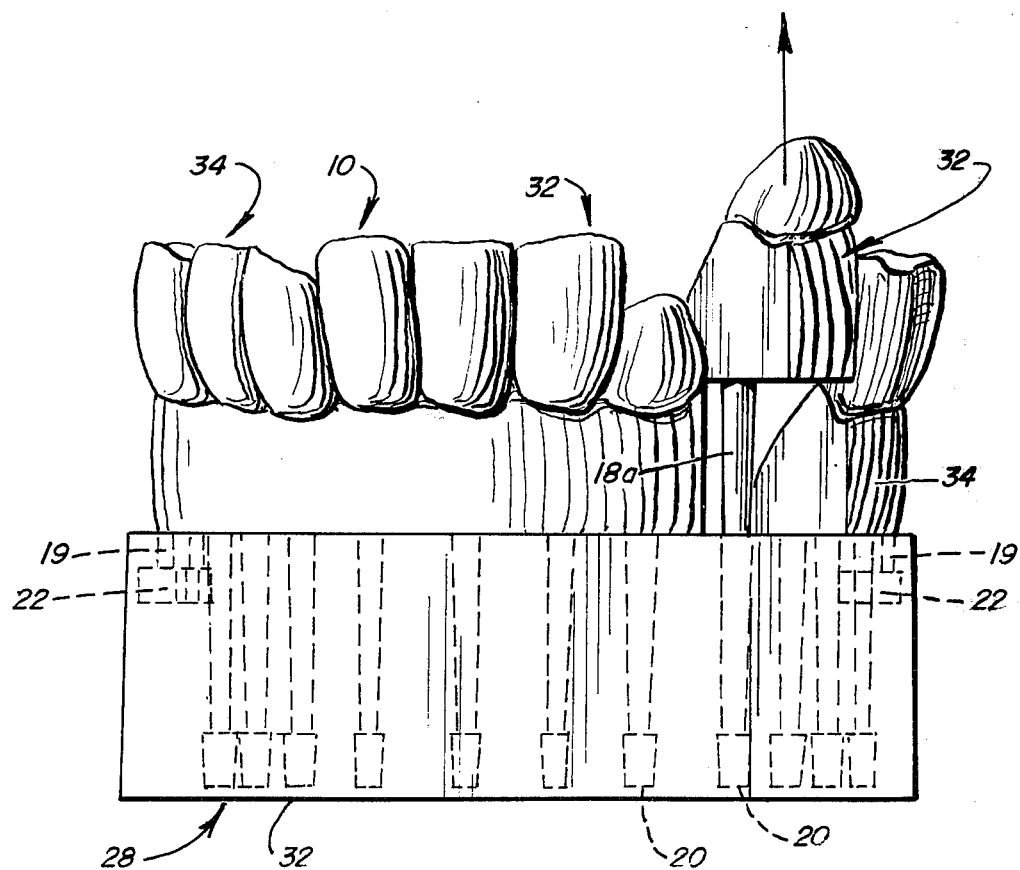
FIG. 5 is an elevational view showing the finished product after grinding of the dental stone to a shape to fit an articulator, and after separate portions of the model have been cut apart, and further showing how certain portions of the model can be removed from the stone.

Removal of the models and the pieces of dental stone upon which they rest preferably takes place while the exothermic phase of curing of the dental stone is still continuing, but after the stone has hardened. The models may be removed by flexing rubber tray 23 as shown in FIG. 5, to break any adhesive bond between the sides of the tray and the dental stone. The die models and blocks of dental stone which carry them may then be lifted out, as FIG. 5 indicates, being broken apart with ease because of the presence of divider partitions 30, so that each die model 10, 10a, 10b, and its associated block of dental stone 28, 28a, and 28b is separated one from the other.

Thereafter, each block of dental stone 28, 28a, and 28b may be ground to fit an articulator, or any other desired use in accordance with conventional dental laboratory techniques. However, as the bottom surface 32 of the stone is ground, colored indicator members 20 are exposed by the grinding prior to reaching the metal dowel pin itself. Accordingly, damaging of the dowel pin with the consequent flaring and adhesion that results may be eliminated because of the presence of indicator members 20. Also, members 20 permit final grinding adjustment after they are exposed, without damaging the dowel pins, since they are typically two or three millimeters thick at their ends and sides.

Each model 10 may be cut transversely, to be separated into individual sections, such as section 32, (FIG. 6), which carries an individual dowel pin 18a. Each of these individual sections, as required, may be removed for work, and then replaced again thereafter. It is typically contemplated that the indicator member 20 associated with dowel pin 18a will usually remain embedded in the dental stone 28.

Sections 34 of model 10, on the other hand, are permanently retained on block 28 by the enlarged head portions 22 of their dowel pins.

As a result, the method and articles of manufacture of this invention provide a significant improvement in the efficiency of dental laboratory operations. Rather than individual, hand-crafted work, as has been conventional in the prior art, this invention permits a single, relatively-unskilled worker to mount several die models in dental stone in the time that it takes a highly-skilled practitioner to produce a single, stone-mounted model. Also, the risk of damaging the dowel pins is significantly reduced as well, while also it becomes possible to permanently retain portions of the model in the stone, while other portions of the same model are temporarily and removably carried thereby.

The above has been offered for illustrative purposes only, and is not intended to limit the scope of this invention, which is as defined in the claims below.

That which is claimed is:

1. The method which comprises filling a flexible tray having sides with uncured, fluid dental stone, to provide a mass of dental stone of predetermined depth; inserting the outer ends of dowel pins carried by a die model into said stone while still in fluid condition, to bring the die model into contact with the surface of said dental stone; at least one of said dowel pins inserted into said dental model being covered with a colored indicating and spacing member; allowing said dental stone to harden; and flexing said flexible tray to remove the dental stone and the die model from it.

2. The method of claim 1 including the step of, after hardening of said dental stone, grinding said dental stone to a desired shape, whereby the uncovering of said colored indicating member by grinding indicates the proximaty of said dowel pin, without damage to the pin.

3. The method of claim 2 in which said colored indicating member comprises colored plastic surrounding the end of said dowel pin.

4. The method of claim 3 in which a plurality of dental die models are placed into contact with the surface of the dental stone, and stiff divider partitions are inserted into said dental stone between the models prior to hardening, whereby said dental stone may be broken up along said divider partitions into separate pieces, to separate said models from each other after hardening.

5. The method of claim 4 in which, prior to filling said flexible tray with uncured fluid dental stone, at least one divider block is placed in said tray to reduce its volume.

6. The method of mounting dental die models on dental stone which comprises:
covering outer ends of dowel pins projecting from a plurality of dental die models with colored indicating members;
filling a flexible tray, having sides, with uncured, fluid, dental stone to provide a mass of dental stone of predetermined depth essentially corresponding to the length of the projecting portions of said dowel pins and indicating members.
inserting the outer ends of the dowel pins of said die models into said stone while still in fluid condition, to bring said die models into contact with the surface of said dental stone;
inserting stiff divider partitions into said dental stone between the die models;
allowing said dental stone to harden;
thereafter flexing said flexible tray to remove the dental stone from it;
breaking up said dental stone along said divider partitions to separate the models from each other; and
grinding said dental stone portions of the models to fit an articulator, whereby the uncovering of said colored indicating members by grinding indicates the proximity of said dowel pins without damage to the pins, and provides further grinding space for adjustment of the plane of occlusion and the like.

7. The method of claim 6 in which said colored indicating members are flexible, transparent plastic pieces surrounding the ends of said dowel pins, and having a thickness of at least 2 mm.

8. The method of claim 7 in which, after said colored indicating members have been applied to the die models, the die models and dowel pins are immersed into a separating medium to reduce adhesion to the dental stone.

9. The method of claim 6 which comprises the prior step of inserting, into portions of said dental die models which are intended to be permanently retained on the dental stone, dowel pins which carry a head member on their outer end, to facilitate permanent retention of the die model portions on the dental stone.

10. The method of claim 6 in which, prior to filling said flexible tray with uncured, fluid dental stone, at least one divider block is placed in said tray to reduce its volume.

11. The method of mounting dental die models on dental stone which comprises: identifying on a dental die model a portion of said die model to be permanently carried by the dental stone; identifying another portion of said die model to be temporarily and removably carried by said dental stone; drilling at least one hole for a dowel pin in the bottom of each said portion of said die model; inserting dowel pins into said holes, the dowel pins of said portion intended for permanent retention carrying a head member on its outer end, and the dowel pins of said portion intended for temporary and removable carrying by the dental stone defining no enlarged head member on its outer end; inserting the outer ends of the dowel pins of said die models into a mass of uncured dental stone to bring the die model into contact with the surface of said dental stone; and thereafter cutting said portions of the die model apart into separate pieces.

12. In a dental die model duplicating at least a portion of a jaw carrying teeth, said die model defining a rear surface and carrying dowel pins protruding from said rear surface, the improvement comprising, in combinations, at least some of said dowel pins having outer ends which carry colored indicating members, whereby upon insertion of said dowel pins into dental stone and subsequent grinding of the stone, said indicator members serve to indicate the proximity of said dowel pins during grinding without damage to the pins, and provide further grinding space for adjustment of the plane of occlusion and the like.

13. The die model of claim 12 in which said colored indicating members comprise colored, transparent plastic surrounding said dowel pin ends.

14. The die model of claim 13 in which a first group of said dowel pins carried by said die model carries said indicating members, and are free of other enlarged portions adjacent their outer ends: and a second group of dowel pins carried by said die model defines enlarged head portions at their ends, integral with said dowel pins, for permanent retention in the dental stone.

15. A dowel pin for use in constructing a dental die model, said dowel pin carrying at its outer end a colored indicating member, whereby upon insertion of said dowel pins in the dental stone and subsequent grinding of the stone, said indicator member serves to indicate the proximity of said dowel pin during grinding without damage to the pin, and provide further grinding space for adjustment of the plane of occlusion and the like.

* * * * *